(12) United States Patent
Katsu et al.

(10) Patent No.: US 11,653,445 B2
(45) Date of Patent: *May 16, 2023

(54) STRETCHABLE MOUNTING BOARD (71) Applicant: Murata Manufacturing Co., Ltd., Nagaokakyo (JP)

(72) Inventors: Hayato Katsu, Nagaokakyo (JP); Keisuke Nishida, Nagaokakyo (JP); Ryo Asai, Nagaokakyo (JP); Takayuki Okada, Nagaokakyo (JP); Shinsuke Tani, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/527,412

(22) Filed: Nov. 16, 2021

(65) Prior Publication Data

US 2022/0078904 A1 Mar. 10, 2022

Related U.S. Application Data

(63) Continuation of application No. 17/070,499, filed on Oct. 14, 2020, now Pat. No. 11,212,915, which is a (Continued)

(30) Foreign Application Priority Data

Mar. 29, 2019 (JP) .............................. JP2019-067973

(51) Int. Cl.
*H05K 1/02* (2006.01)
*H05K 1/03* (2006.01)
(Continued)

(52) U.S. Cl.
CPC ......... *H05K 1/0283* (2013.01); *H05K 1/0393* (2013.01); *H05K 1/111* (2013.01); (Continued)

(58) Field of Classification Search
CPC .... H05K 1/0283; H05K 1/0393; H05K 1/111; H05K 1/181; H05K 1/0277; H05K 1/092; (Continued)

(56) References Cited

U.S. PATENT DOCUMENTS 7,268,437 B2 9/2007 Liu
7,425,683 B2* 9/2008 Kurihara ........... H01L 23/49582
174/257
(Continued)

FOREIGN PATENT DOCUMENTS

JP 2002042548 A 2/2002
JP 2007300038 A 11/2007
(Continued)

OTHER PUBLICATIONS

International Search Report issued for PCT/JP2020/010718, dated Jun. 2, 2020.

*Primary Examiner* — Ishwarbhai B Patel
(74) *Attorney, Agent, or Firm* — ArentFox Schiff LLP (57) ABSTRACT

A stretchable mounting board that includes a stretchable substrate having a main surface, a stretchable wiring disposed on the main surface of the stretchable substrate, a mounting electrode section electrically connected to the stretchable wiring, solder electrically connected to the mounting electrode section and including bismuth and tin, and an electronic component electrically connected to the mounting electrode section with the solder interposed therebetween. The mounting electrode section has a first electrode layer on a side thereof facing the stretchable wiring and which includes bismuth and tin, and a second electrode layer on a side thereof facing the solder and which includes bismuth and tin. A concentration of the bismuth in the first electrode layer is lower than a concentration of the bismuth in the second electrode layer.

20 Claims, 9 Drawing Sheets

Related U.S. Application Data continuation of application No. PCT/JP2020/010718, filed on Mar. 12, 2020.

(51) Int. Cl.
  *H05K 1/11* (2006.01)
  *H05K 1/18* (2006.01)
  *H05K 1/09* (2006.01)

(52) U.S. Cl.
  CPC ........... *H05K 1/181* (2013.01); *H05K 1/0277* (2013.01); *H05K 1/092* (2013.01); *H05K 1/095* (2013.01); *H05K 2203/0405* (2013.01)

(58) Field of Classification Search
  CPC ........... H05K 1/095; H05K 2203/0405; H05K 2201/0266; H05K 3/3485; H05K 2201/0269; H05K 2201/0352; H05K 3/245; H05K 3/3463; H05K 2201/0338; H05K 2201/035; H05K 2201/0379; H05K 2201/09372; A61B 2562/125; A61B 2562/164; A61B 5/263; A61B 5/25
  See application file for complete search history.

(56) References Cited

U.S. PATENT DOCUMENTS

| | | | |
|---|---|---|---|
| 3,039,760 | A1 | 10/2011 | Sagawa et al. |
| 10,264,673 | B2 | 4/2019 | Kanda et al. |
| 11,212,915 | B2* | 12/2021 | Katsu .................. A61B 5/25 |
| 2010/0258341 | A1 | 10/2010 | Sagawa et al. |
| 2018/0027661 | A1 | 1/2018 | Ogura |
| 2018/0249576 | A1 | 8/2018 | Ogura |
| 2019/0232438 | A1 | 8/2019 | Hino et al. |

FOREIGN PATENT DOCUMENTS

| | | |
|---|---|---|
| JP | 2015153997 A | 8/2015 |
| WO | 2009081929 A1 | 7/2009 |

* cited by examiner

FIG. 11

STRETCHABLE MOUNTING BOARD

CROSS REFERENCE TO RELATED APPLICATIONS

The present application is a continuation of application Ser. No. 17/070,499, filed Oct. 14, 2020, now U.S. Pat. No. 11,212,915, which is a continuation of International application No. PCT/JP2020/010718, filed Mar. 12, 2020, which claims priority to Japanese Patent Application No. 2019-067973, filed Mar. 29, 2019, the entire contents of each of which are incorporated herein by reference.

FIELD OF THE INVENTION

The present invention relates to a stretchable mounting board.

BACKGROUND OF THE INVENTION

In recent years, a wiring board has been used to manage a state and the like of a living body (for example, a human body) by acquiring and analyzing biological information.

An electronic component may be mounted on such a wiring board. For example, Patent Document 1 discloses a mounting board in which an electronic component is mounted on an insulating substrate with solder and a conductor interposed therebetween.

Patent Document 1: International Publication No. 2009/081929

SUMMARY OF THE INVENTION

A mounting board in which an electronic component is mounted is required to have stretchability capable of following a movement of a living body when attached to the living body. As a constituent material of wiring of the mounting board having such stretchability, for example, a mixture of conductive particles and a resin is used. When the electronic component is connected to such wiring with solder interposed therebetween, the wiring and the solder may react with each other to generate a brittle metal compound. Therefore, when the mounting board expands or contracts, the wiring is likely to be disconnected in a region where the brittle metal compound is generated.

Patent Document 1 does not disclose that the mounting board has stretchability. Further, a second conductor that is in contact with the solder is configured by a member including copper. Wettability of the solder with respect to the second conductor is insufficient, and thus an electrical and mechanical connection between the solder and the second conductor is insufficient.

The present invention has been made to solve the above problems. An object of the present invention is to provide a stretchable mounting board that can suppress a disconnection of stretchable wiring during expansion and contraction when an electronic component is connected to the stretchable wiring with solder interposed therebetween, while ensuring an electrical and mechanical connection.

A stretchable mounting board of the present invention includes a stretchable substrate having a main surface, a stretchable wiring disposed on the main surface of the stretchable substrate, a mounting electrode section electrically connected to the stretchable wiring, solder electrically connected to the mounting electrode section and including bismuth and tin, and an electronic component electrically connected to the mounting electrode section with the solder interposed therebetween. The mounting electrode section has a first electrode layer on a side thereof facing the stretchable wiring and which includes bismuth and tin, and a second electrode layer on a side thereof facing the solder and which includes bismuth and tin. A concentration of the bismuth in the first electrode layer is lower than a concentration of the bismuth in the second electrode layer.

The stretchable mounting board of the present invention can suppress a disconnection of stretchable wiring during expansion and contraction when an electronic component is connected to the stretchable wiring with solder interposed therebetween, thus ensuring an electrical and mechanical connection.

DETAILED DESCRIPTION OF THE INVENTION

A stretchable mounting board of the present invention will be described below. The present invention is not limited to the following configurations, and may be modified as appropriate without departing from the gist of the present invention. Further, a combination of a plurality of individual preferable configurations described below is also the present invention.

In the present specification, a "thickness" means a length in a direction perpendicular to a surface of the stretchable substrate in a sectional view. Further, the "thickness" is indicated as in a state where the stretchable mounting board is not stretched unless otherwise specified.

[Stretchable Mounting Board]

Figure 1:
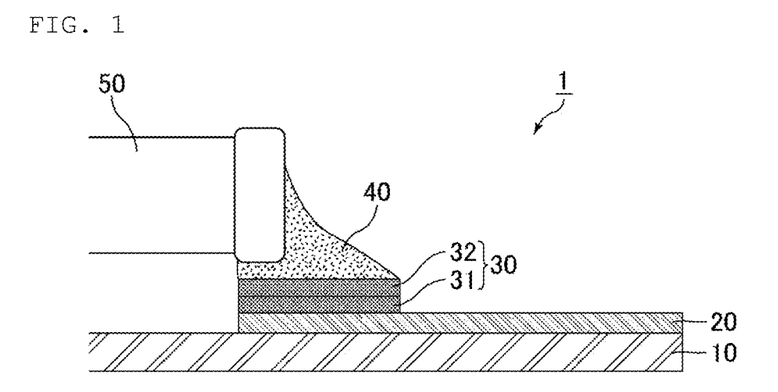
FIG. 1 is a schematic sectional view showing one example of a stretchable mounting board of the present invention.

FIG. 1 is a schematic sectional view showing one example of a stretchable mounting board of the present invention. As shown in FIG. 1, the stretchable mounting board 1 has a stretchable substrate 10, stretchable wiring 20, a mounting electrode section 30, solder 40, and an electronic component 50.

<Stretchable Substrate>

The stretchable substrate 10 preferably includes at least one resin selected from the group consisting of a silicone resin, an acrylic resin, an olefin resin, and a urethane resin. Examples of the urethane resins include thermoplastic polyurethane.

When the stretchable mounting board 1 is attached to a living body, a thickness of the stretchable substrate 10 is preferably 100 µm or less, and more preferably 50 µm or less, so as not to inhibit expansion and contraction of a surface of the living body. Further, the thickness of the stretchable substrate 10 is preferably 10 µm or more.

<Stretchable Wiring>

The stretchable wiring 20 is disposed on one main surface of the stretchable substrate 10.

Examples of constituent materials of the stretchable wiring 20 include a mixture of conductive particles and a resin. Above all, the stretchable wiring 20 preferably includes silver as conductive particles and a resin.

In addition to silver, examples of the conductive particles include copper and nickel. An average particle diameter of the conductive particles is preferably 0.01 µm to 10 µm. A shape of the conductive particles is preferably spherical.

The resin preferably includes at least one resin (elastomer resin) selected from the group consisting of an epoxy resin, a urethane resin, an acrylic resin, and a silicone resin.

A thickness of the stretchable wiring 20 is preferably 100 µm or less, and more preferably 50 µm or less. Further, the thickness of the stretchable wiring 20 is preferably 1 µm or more.

<Mounting Electrode Section>

The mounting electrode section 30 is connected to the stretchable wiring 20. More specifically, the mounting electrode section 30 is in contact with a side of the stretchable wiring 20 opposite to the stretchable substrate 10.

The mounting electrode section 30 includes silver, bismuth, tin, and a resin. The mounting electrode section 30 may include another metal such as copper, aluminum, or nickel in addition to silver, bismuth, and tin. The mounting electrode section 30 may include a metal such as copper, aluminum, or nickel instead of silver. For example, the mounting electrode section 30 may include copper, bismuth, tin, or a resin. As the resin included in the mounting electrode section 30, a resin (elastomer resin) such as an epoxy resin, a urethane resin, an acrylic resin, a silicone resin, a polyester resin, or the like can be used.

The mounting electrode section 30 has a first electrode layer 31 on a side thereof facing the stretchable wiring 20 and a second electrode layer 32 on a side thereof facing the solder 40.

A concentration of the bismuth in the first electrode layer 31 is lower than a concentration of the bismuth in the second electrode layer 32, and is constant along a thickness direction thereof. It can be said that in the mounting electrode section 30, bismuth is densely distributed in the second electrode layer 32, but is not densely distributed in the first electrode layer 31 as a whole.

In the stretchable mounting board 1, although the solder 40 includes bismuth, the second electrode layer 32 in which bismuth is densely distributed is disposed on the side thereof facing the solder 40 in the mounting electrode section 30 as will be described later. Thus, wettability of the solder 40 with respect to the second electrode layer 32 is good, and an electrical and mechanical connection between the second electrode layer 32 and the solder 40 is secured.

In a conventional stretchable mounting board that does not have the mounting electrode section 30, when the stretchable wiring 20 includes a mixture of conductive particles and a resin, the stretchable wiring 20 reacts with the solder 40 to generate a brittle metal compound which will be a starting point of disconnection of the stretchable wiring 20 during expansion and contraction. As will be described later, the solder 40 includes bismuth, and this brittle metal compound includes bismuth diffused from the solder 40.

On the other hand, in the stretchable mounting board 1 of the present invention, the first electrode layer 31 in which bismuth is not densely distributed in the mounting electrode section 30 is disposed on the side thereof facing the stretchable wiring 20. Thus, a brittle metal compound as in the conventional stretchable mounting board is not generated, and a disconnection of the stretchable wiring 20 is suppressed when the stretchable mounting board 1 expands and contracts.

The concentration of bismuth in the first electrode layer 31 and the second electrode layer 32 is determined from a concentration distribution obtained by cross-section profiling in the thickness direction with respect to the mapping diagram of each element by a scanning electron microscope-energy dispersive X-ray spectroscopy (SEM-EDS). "The concentration is constant along a thickness direction" described herein means that a rate of change of the concentration is within ±5% over a range of 5 µm or more along the thickness direction.

A bismuth eutectic size in the second electrode layer 32 is preferably larger than a bismuth eutectic size in the first electrode layer 31. In this case, it can be said that the concentration of bismuth in the first electrode layer 31 is considerably lower than the concentration of bismuth in the second electrode layer 32. Thus, the electrical and mechanical connection between the second electrode layer 32 and the solder 40 is sufficiently ensured. Further, an action of the first electrode layer 31 sufficiently suppresses a disconnection of the stretchable wiring 20 when the stretchable mounting board 1 expands and contracts.

The bismuth eutectic size in the second electrode layer 32 is preferably 1 µm or more.

The bismuth eutectic size in the first electrode layer 31 and the bismuth eutectic size in the second electrode layer 32 are determined as follows. First, the cross-sections of the first electrode layer 31 and the second electrode layer 32 of the stretchable mounting board 1 are exposed by polishing. Then, bismuth-rich eutectic parts in the electrode layers are binarized using image analysis software, and then an area is determined, and an equivalent circle diameter is calculated. This circle equivalent diameter is determined as a particle diameter of the bismuth eutectic part. As the image analysis software, "Photoshop" manufactured by Adobe Systems Incorporated is used. Then, distribution of the particle diameter is calculated, and a particle diameter at a frequency of 50% is determined as an average particle diameter. The average particle diameter thus obtained in each electrode layer is determined as the bismuth eutectic size.

A concentration of the tin in the first electrode layer 31 is preferably lower than the concentration of the tin in the second electrode layer 32.

A thickness of the first electrode layer 31 is preferably 5 µm or more, and more preferably 10 µm or more. In this case, the second electrode layer 32 in which the bismuth is densely distributed and the stretchable wiring 20 are sufficiently apart from each other, and therefore a disconnection of the stretchable wiring 20 is sufficiently suppressed when the stretchable mounting board 1 expands and contracts. The thickness of the first electrode layer 31 of 5 μm or more suggests that the first electrode layer 31 has been formed by a screen printing method, an inkjet method, a dispenser method, or the like. The thickness of the first electrode layer 31 is preferably 40 μm or less, and more preferably 30 μm or less.

A thickness of the second electrode layer 32 is preferably 5 μm or more. In this case, an electrical and mechanical connection between the second electrode layer 32 and the solder 40 is sufficiently ensured. The thickness of the second electrode layer 32 of 5 μm or more suggests that the second electrode layer 32 has been formed by the screen printing method, the inkjet method, the dispenser method, or the like. The thickness of the second electrode layer 32 is preferably 20 μm or less, and more preferably 10 μm or less.

The thickness of the first electrode layer 31 and the thickness of the second electrode layer 32 may be the same or different.

Figure 2:
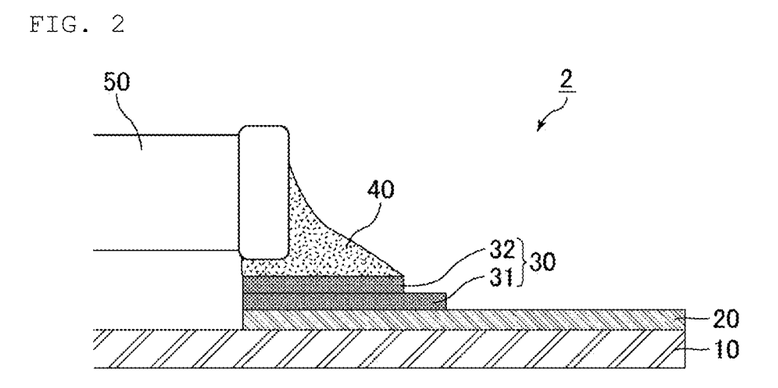
FIG. 2 is a schematic sectional view showing another example of the stretchable mounting board of the present invention.

FIG. 2 is a schematic sectional view showing another example of the stretchable mounting board of the present invention. As in a stretchable mounting board 2 shown in FIG. 2, the length of the first electrode layer 31 may be larger than a length of the second electrode layer 32 in a direction parallel to the surface of the stretchable substrate 10. In this case, the second electrode layer 32 in which the bismuth is densely distributed and the stretchable wiring 20 are sufficiently apart from each other with the first electrode layer 31 interposed therebetween. A disconnection of the stretchable wiring 20 is therefore sufficiently suppressed when the stretchable mounting board 2 expands and contracts.

Figure 3:
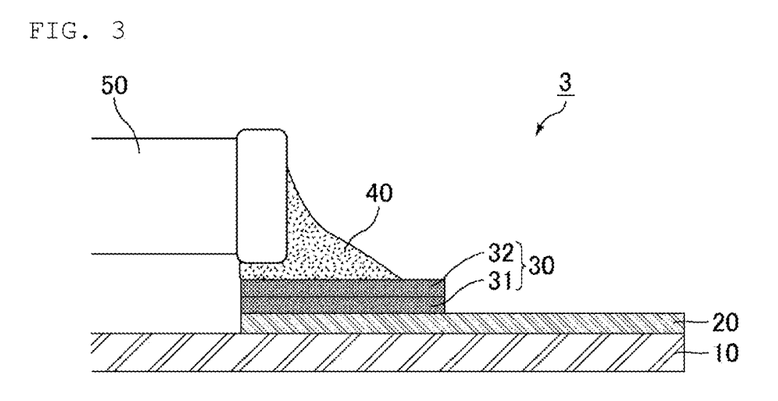
FIG. 3 is a schematic sectional view showing still another example of the stretchable mounting board of the present invention.

FIG. 3 is a schematic sectional view showing still another example of the stretchable mounting board of the present invention. As in a stretchable mounting board 3 shown in FIG. 3, the length of the mounting electrode section 30 may be larger than a length of a part of the solder 40 that is connected to the mounting electrode section 30 in the direction parallel to the surface of the stretchable substrate 10. In this case, it is possible to prevent the stretchable wiring 20 and the solder 40 from reacting with each other to generate a brittle metal compound which will be a starting point of a disconnection of the stretchable wiring 20 during expansion and contraction.

<Solder>

The solder 40 is connected to the mounting electrode section 30. More specifically, the solder 40 is in contact with a side of the mounting electrode section 30 (second electrode layer 32) opposite to the stretchable wiring 20.

The solder 40 includes bismuth and tin and is also referred to as a so-called low temperature solder. Thus, when the solder 40 is used, soldering can be performed without damaging the electronic component 50, the stretchable substrate 10 including a resin, and the stretchable wiring 20.

<Electronic Component>

The electronic component 50 is connected to the mounting electrode section 30 with the solder 40 interposed therebetween.

Examples of the electronic component 50 include an amplifier (operation amplifier, transistor, and the like), a diode, an integrated circuit (IC), a capacitor, a resistor, and an inductor.

The stretchable mounting board 1 may have an electrode connected to the stretchable wiring 20 at a position different from the mounting electrode section 30. The stretchable mounting board 1 can be used as a sensor by being attached to a living body with an electrode interposed therebetween.

The electrode is preferably a gel electrode. Interposing the gel electrode allows the stretchable mounting board 1 to be attached to the living body. The gel electrode is configured by a conductive gel material including, for example, water, alcohol, a moisturizer, and an electrolyte. Examples of such gel material include hydrogel.

[Method of Manufacturing Stretchable Mounting Board]

The stretchable mounting board 1 is manufactured as follows, for example.

(1) Formation of Stretchable Wiring

A conductive paste for stretchable wiring (for example, a conductive paste including a mixture of silver and a resin) is printed on the one main surface of the stretchable substrate 10 by using the screen printing method or the like. Then, the stretchable wiring 20 is formed by thermosetting the conductive paste for stretchable wiring so as to obtain a predetermined resistance value.

(2) Formation of Mounting Electrode Section

A conductive paste for the first electrode layer (for example, a conductive paste including a mixture of silver and a resin) is printed on the side of the stretchable wiring 20 opposite to the stretchable substrate 10 by using the screen printing method or the like. A solvent concentration of the conductive paste for the first electrode layer is, for example, 6% by weight or less. Then, the first electrode layer 31 is formed by thermosetting the conductive paste for the first electrode layer.

Next, a conductive paste for the second electrode layer (for example, a conductive paste including a mixture of silver and a resin) having a solvent concentration higher than the solvent concentration of the conductive paste for the first electrode layer is printed on a side of the first electrode layer 31 opposite to the stretchable wiring 20 by using the screen printing method or the like. The solvent concentration of the conductive paste for the second electrode layer is, for example, 10% by weight or more. Then, the second electrode layer 32 is formed by thermosetting the conductive paste for the second electrode layer.

Examples of the solvent in the conductive paste for the first electrode layer and the conductive paste for the second electrode layer include terpineol.

The mounting electrode section 30 configured by the first electrode layer 31 and the second electrode layer 32 is formed as described above. The first electrode layer 31 has a denser structure than the second electrode layer 32 due to a difference in the solvent concentration of the used conductive paste.

(3) Mounting of Electronic Component

The solder 40 is printed on the side of the mounting electrode section 30 (second electrode layer 32) opposite to the stretchable wiring 20 by using a metal mask or the like. Subsequently, the electronic component 50 is mounted on the solder 40, and then is heated in a reflow furnace. As described above, the electronic component 50 is connected to the mounting electrode section 30 with the solder 40 interposed therebetween.

By being heated in the reflow furnace, the bismuth and tin in the solder 40 diffuse (permeate) in the second electrode layer 32 of the mounting electrode section 30. This is related to the fact that the second electrode layer 32 does not have a dense structure. Therefore, the wettability of the solder 40 with respect to the second electrode layer 32 becomes good, and the electrical and mechanical connection between the second electrode layer 32 and the solder 40 is secured.

On the other hand, of the bismuth and tin diffused in the second electrode layer 32, tin having a high diffusion rate diffuses to some extent in the first electrode layer 31, but bismuth having a slow diffusion rate does not easily diffuse in the first electrode layer 31. The reason for the bismuth not to easily diffuse in the first electrode layer 31 has something to do with the first electrode layer 31 having a dense structure.

In the conventional stretchable mounting board that does not have the mounting electrode section 30, when the stretchable wiring 20 includes a mixture of conductive particles and a resin, heat treatment in a reflow furnace during mounting of the electronic component 50 causes a reaction between the stretchable wiring 20 and the solder 40 to generate a brittle metal compound which will be a starting point of a disconnection of the stretchable wiring 20 during expansion and contraction. This brittle metal compound includes bismuth diffused from the solder 40.

On the other hand, in the stretchable mounting board 1, the first electrode layer 31 suppresses the diffusion of bismuth from the solder 40 to the stretchable wiring 20. Thus, a conventional brittle metal compound is not generated, and a disconnection of the stretchable wiring 20 is suppressed when the stretchable mounting board 1 expands and contracts.

EXAMPLES

Hereinafter, examples more specifically disclosing the stretchable mounting board of the present invention will be described. Note that the present invention is not limited to only these examples.

Example 1

A stretchable mounting board of Example 1 was manufactured as follows.
(1) Formation of Stretchable Wiring
A conductive paste for stretchable wiring including a mixture of silver and a urethane resin was printed on one main surface of a stretchable substrate including thermoplastic polyurethane by a screen printing method. After that, a stretchable wiring was formed by thermosetting the printed conductive paste.
(2) Formation of Mounting Electrode Section
A conductive paste for a first electrode layer including a mixture of silver and a polyester resin and having a solvent concentration of 6% by weight was printed on a side of the stretchable wiring opposite to the stretchable substrate by using the screen printing method. Terpineol was used as a solvent in the conductive paste for the first electrode layer. Then, the first electrode layer was formed by thermosetting the conductive paste for the first electrode layer.

Next, a conductive paste for a second electrode layer including a mixture of silver and a polyester resin and having a solvent concentration of 10% by weight was printed on a side of the stretchable wiring opposite to the first electrode layer by using the screen printing method. Terpineol was used as the solvent in the conductive paste for the second electrode layer. Then, the second electrode layer was formed by thermosetting the conductive paste for the second electrode layer.

As described above, a mounting electrode section configured by the first electrode layer and the second electrode layer was formed.
(3) Mounting of Electronic Component
Solder including bismuth and tin was printed on a side of the mounting electrode section (second electrode layer) opposite to the stretchable wiring by using a metal mask. Subsequently, an electronic component was mounted on the solder, and then was heated in a reflow furnace. As described above, the electronic component was connected to the mounting electrode section with the solder interposed therebetween.

As described above, the stretchable mounting board of Example 1 was completed.

Comparative Example 1

A stretchable mounting board of Comparative Example 1 was manufactured in a similar manner to the stretchable mounting board of Example 1 except that the mounting electrode section was not formed.

Comparative Example 2

A stretchable mounting board of Comparative Example 2 was manufactured in a similar manner to the stretchable mounting board of Example 1 except that the solvent concentration in the conductive paste for the first electrode layer was 10% by weight. That is, in the stretchable mounting board of Comparative Example 2, the mounting electrode section had a one-layer structure instead of a two-layer structure.

<Evaluation 1>

A cross section of the stretchable mounting board of Example 1 was exposed by polishing, and then mapping of each element was performed using a scanning electron microscope-energy dispersive X-ray spectroscopy (SEM-EDS). Subsequently, a concentration distribution of each element was obtained by cross-section profiling in a thickness direction with respect to the obtained mapping diagram of each element.

Figure 4:
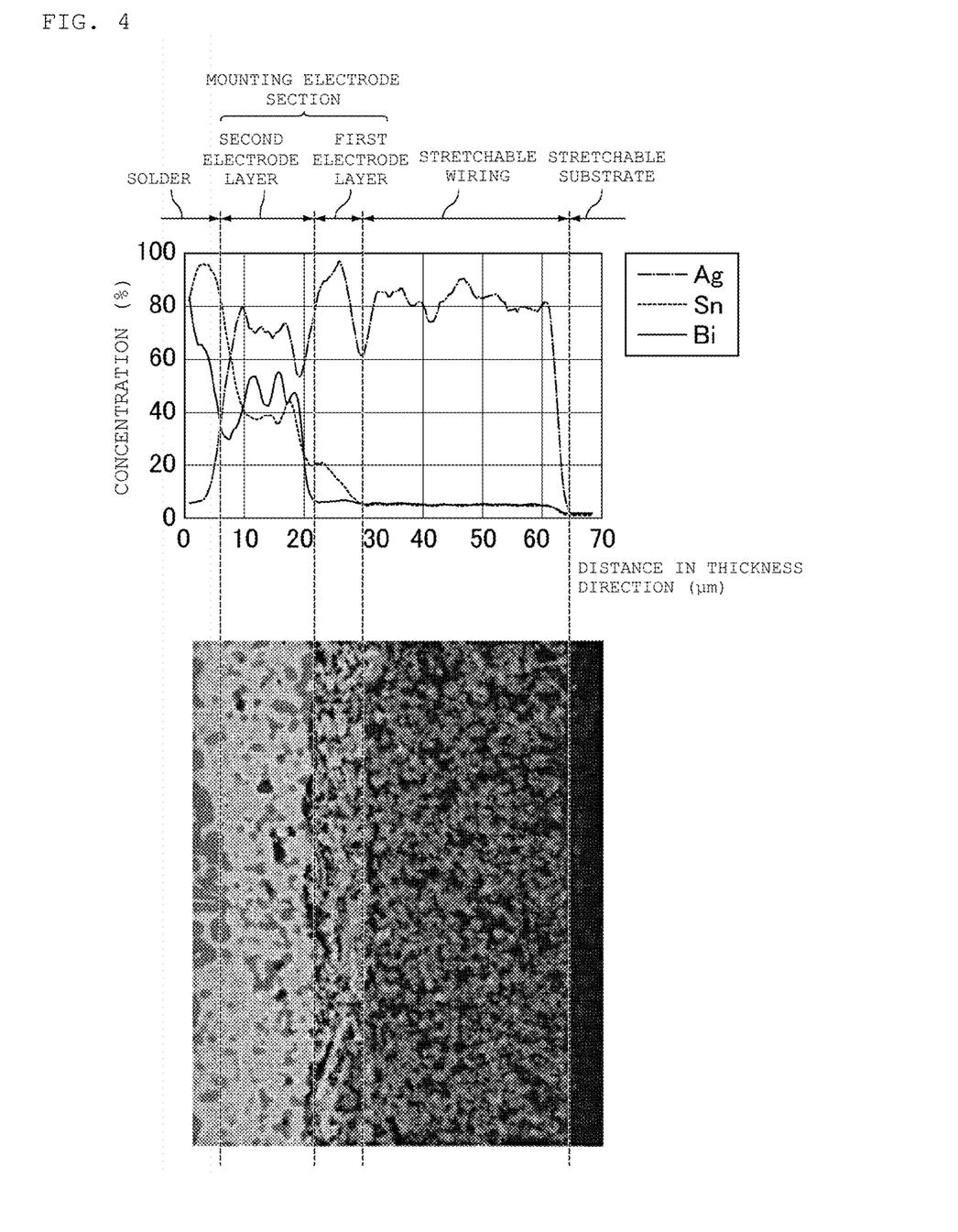
FIG. 4 is a diagram showing a correspondence relationship between a graph of concentration distribution of elements and a mapping diagram of the elements in the stretchable mounting board of Example 1.
Figure 5:
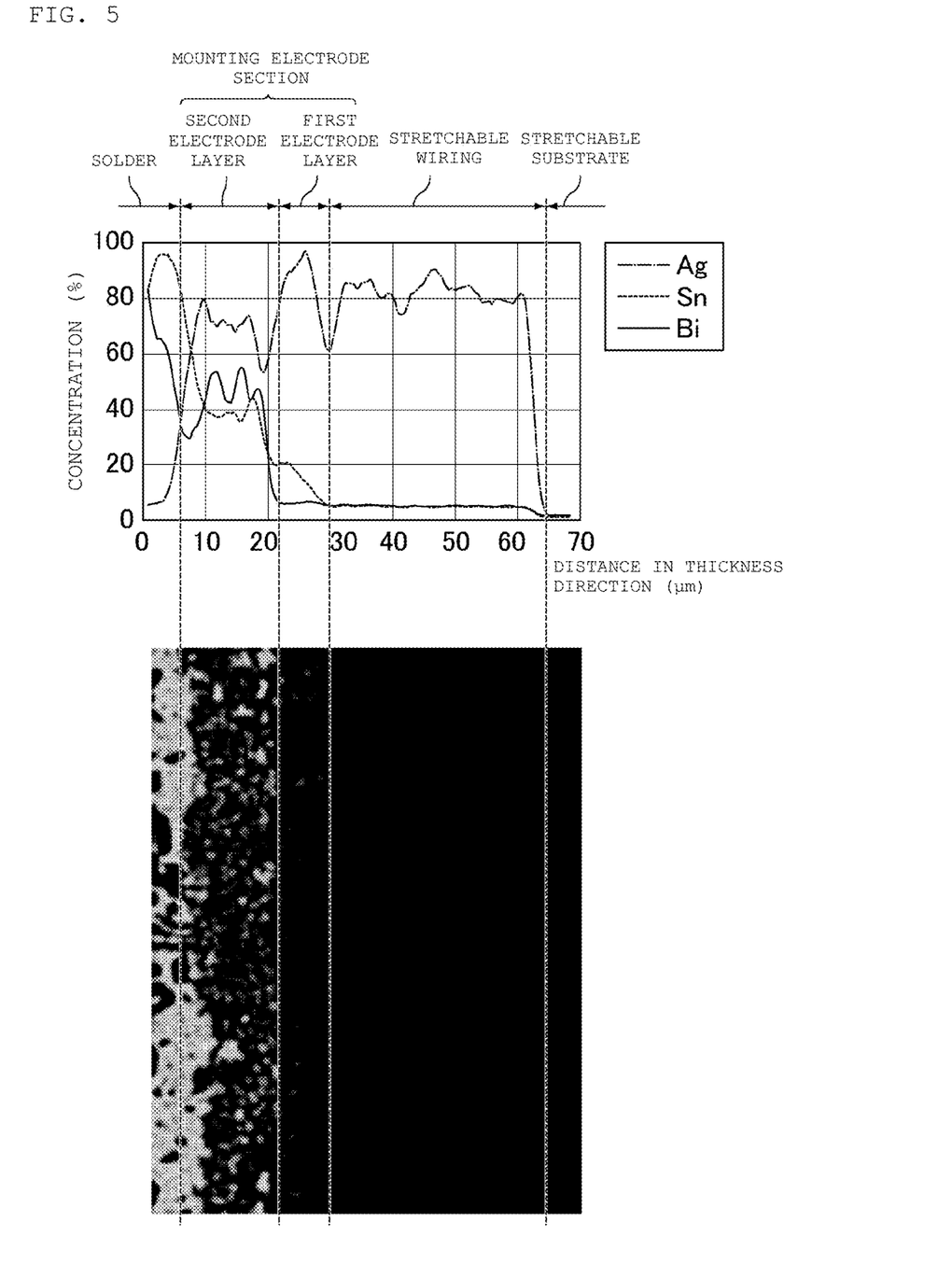
FIG. 5 is a diagram focusing on tin in the mapping diagram in FIG. 4.
Figure 6:
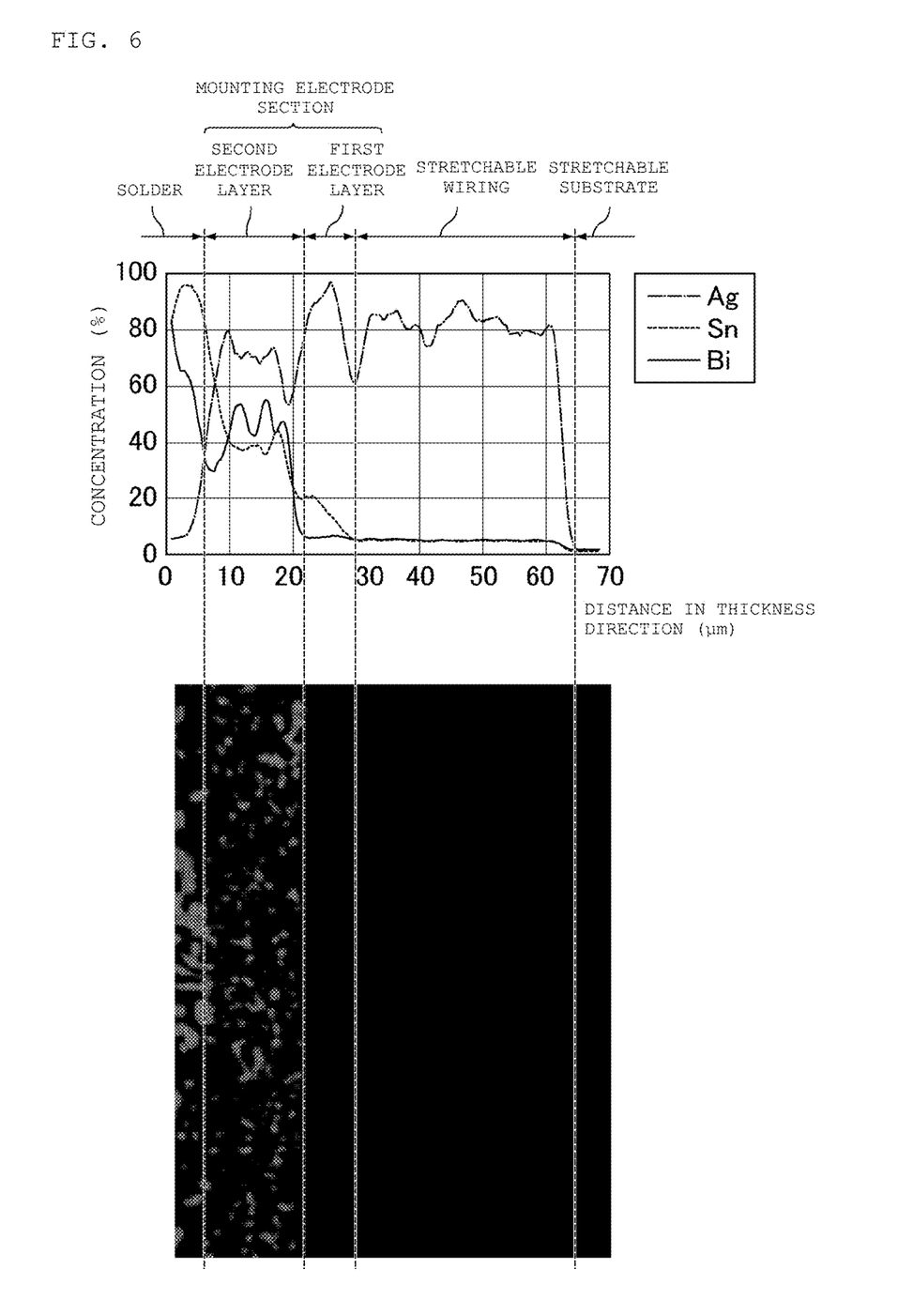
FIG. 6 is a diagram focusing on bismuth in the mapping diagram in FIG. 4.

FIG. 4 is a diagram showing a correspondence relationship between a graph of concentration distribution of elements and the mapping diagram of the elements in the stretchable mounting board of Example 1. FIG. 5 is a diagram focusing on tin in the mapping diagram in FIG. 4. FIG. 6 is a diagram focusing on bismuth in the mapping diagram in FIG. 4. The "concentration" (unit: %) indicated by a vertical axis of the graphs in FIGS. 4, 5, and 6 is standardized with a maximum concentration of each element being 100%. "A distance in the thickness direction" (unit: μm) indicated by a horizontal axis of the graphs in FIGS. 4, 5, and 6 is a thickness direction from a vicinity of an interface between the solder and the mounting electrode section toward the stretchable substrate. Note that, in the graphs in FIGS. 4, 5, and 6, the concentration distribution of silver (Ag), tin (Sn), and bismuth (Bi) is shown as a representative among the elements configuring the stretchable mounting board of Example 1.

As shown in the mapping diagram in FIG. 4, in the stretchable mounting board of Example 1, a boundary between the stretchable wiring and the mounting electrode section was identified, and it was also confirmed that the mounting electrode section was a two-layer structure having the first electrode layer and the second electrode layer.

As shown in the graph in FIG. 4, bismuth and tin in the solder diffused in the second electrode layer in the stretchable mounting board of Example 1. It was therefore observed that wettability of the solder with respect to the second electrode layer became good, and an electrical and mechanical connection between the second electrode layer and the solder was secured. On the other hand, although diffusion of tin was observed from the second electrode layer to the first electrode layer, diffusion of bismuth was suppressed. As a result, the concentration of the bismuth in the first electrode layer was lower than the concentration of the bismuth in the second electrode layer, and was constant along the thickness direction. Further, diffusion of both tin and bismuth from the first electrode layer to the stretchable wiring was suppressed.

A state where tin in the solder diffused in the second electrode layer and the first electrode layer sequentially was confirmed from the mapping diagram (focusing on tin) in FIG. 5. Further, a state where the bismuth in the solder diffused in the second electrode layer, but not easily diffused in the first electrode layer was confirmed from the mapping diagram in FIG. 6 (focusing on bismuth). In the mapping diagram (focusing on bismuth) in FIG. 6, it is difficult to confirm a presence or absence of bismuth in the first electrode layer, but a presence of bismuth in the first electrode layer was confirmed as can be seen from the graph in FIG. 6. It was also confirmed that a bismuth eutectic size in the first electrode layer was smaller than a bismuth eutectic size in the second electrode layer.

<Evaluation 2>

A resistance of the stretchable wiring of the stretchable mounting boards of Example 1 and Comparative Example 1 was measured while changing an expansion ratio. For the measurement, a plurality of the stretchable mounting boards of Example 1 and a plurality of the stretchable mounting boards of Comparative Example 1 were used.

Figure 7:
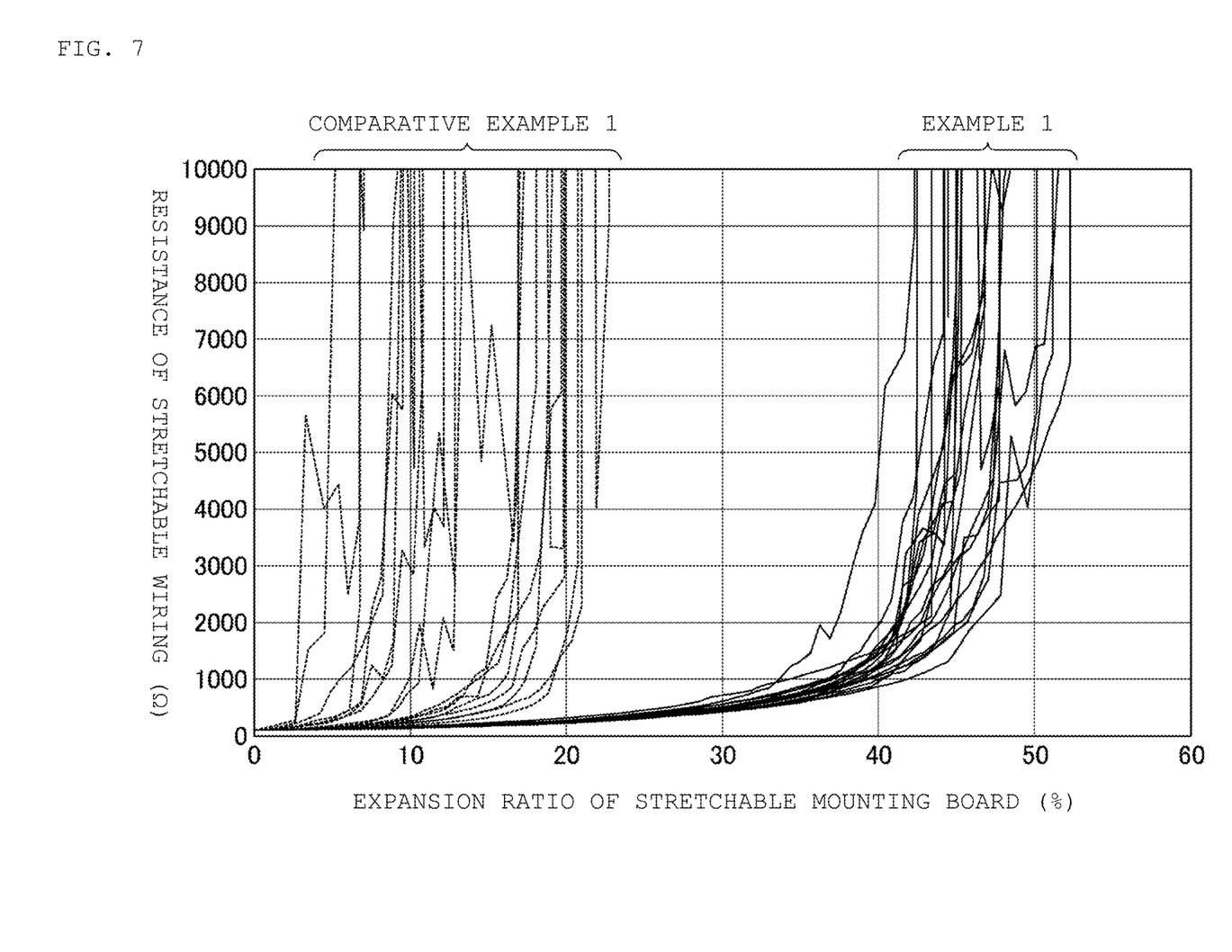
FIG. 7 is a graph showing a relationship between an expansion ratio and a resistance of stretchable wiring of the stretchable mounting boards of Example 1 and Comparative Example 1.

FIG. 7 is a graph showing a relationship between the expansion ratio and the resistance of stretchable wiring of the stretchable mounting boards of Example 1 and Comparative Example 1. As shown in FIG. 7, an increase in the resistance of the stretchable wiring due to the expansion of the stretchable mounting board was suppressed in the stretchable mounting board of Example 1 more than in the stretchable mounting board of Comparative Example 1. Further, the resistance of the stretchable wiring starts to rise sharply, which is considered to indicate that the stretchable wiring starts to be disconnected. However, a disconnection of the stretchable wiring during the expansion of the stretchable mounting board was suppressed in the stretchable mounting board of Example 1 more than in the stretchable mounting board of Comparative Example 1. More specifically, as a range of the expansion ratio in which the stretchable wiring is not considered to be disconnected, the stretchable mounting board of Example 1 could expand to about 40%, whereas the stretchable mounting board of Comparative Example 1 could expand up to only about 20%. As a result of actual observation, in the stretchable mounting board of Comparative Example 1, the stretchable wiring and the solder reacted with each other to generate a brittle metal compound including bismuth.

<Evaluation 3>

A cross section of the stretchable mounting board of Comparative Example 2 was exposed by polishing, and then mapping of each element was performed using the scanning electron microscope-energy dispersive X-ray spectroscopy (SEM-EDS). Subsequently, a concentration distribution of each element was obtained by cross-section profiling in a thickness direction with respect to the obtained mapping diagram of each element.

Figure 8:
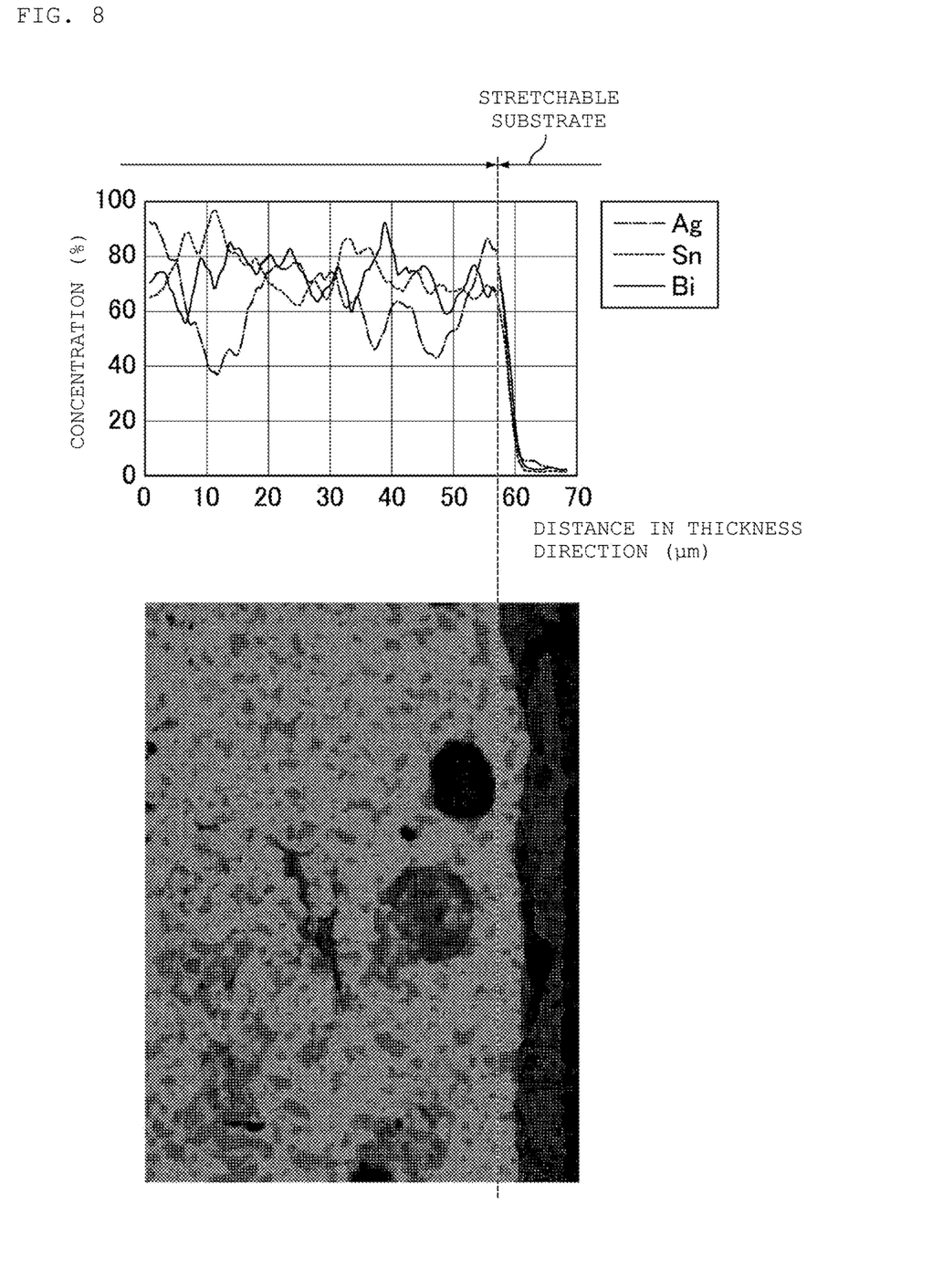
FIG. 8 is a diagram showing a correspondence relationship between a graph of concentration distribution of elements and a mapping diagram of the elements in a stretchable mounting board of Comparative Example 2.
Figure 9:
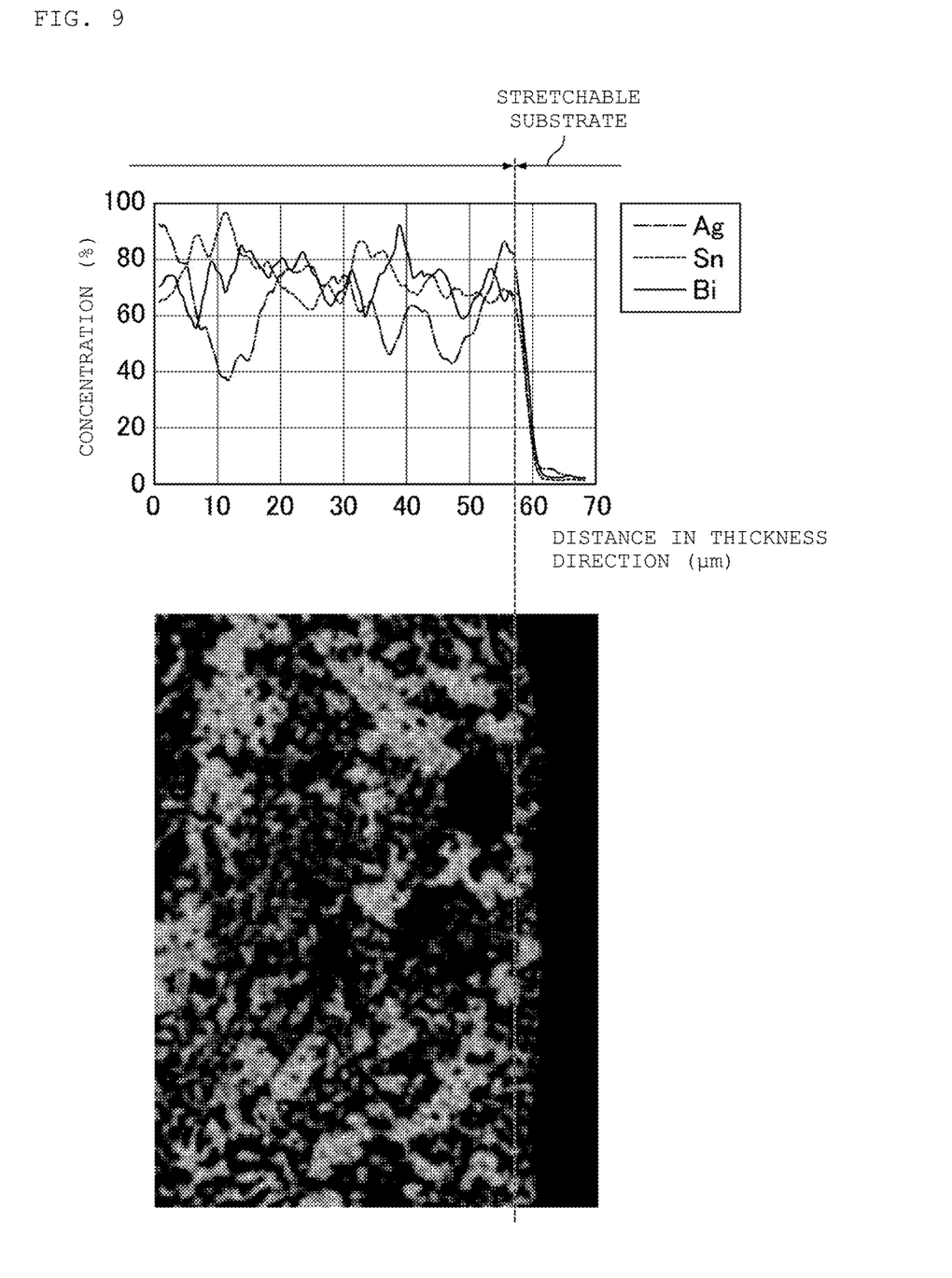
FIG. 9 is a diagram focusing on tin in the mapping diagram in FIG. 8.
Figure 10:
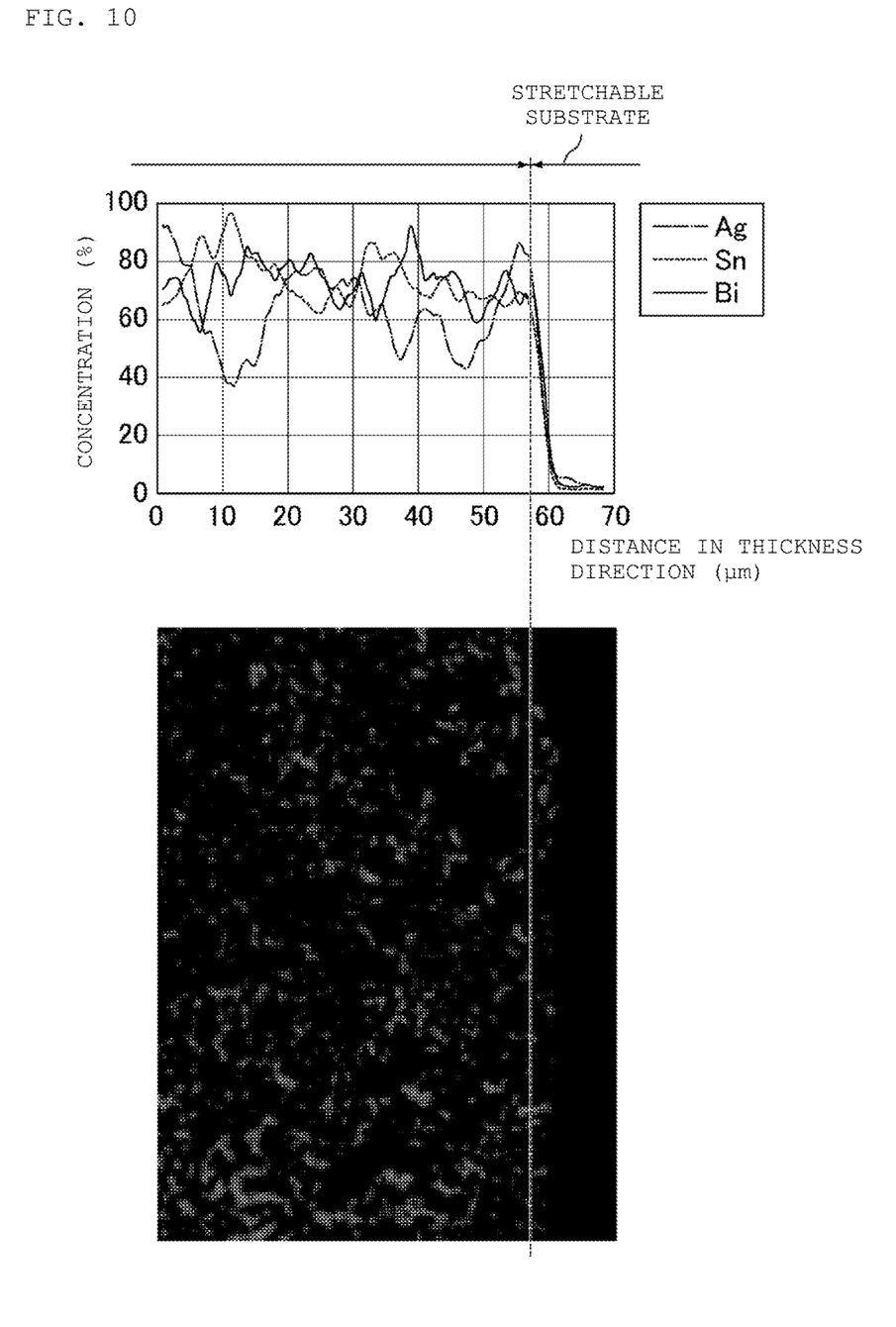
FIG. 10 is a diagram focusing on bismuth in the mapping diagram in FIG. 8.

FIG. 8 is a diagram showing a correspondence relationship between a graph of concentration distribution of elements and the mapping diagram of the elements in the stretchable mounting board of Comparative Example 2. FIG. 9 is a diagram focusing on tin in the mapping diagram in FIG. 8. FIG. 10 is a diagram focusing on bismuth in the mapping diagram in FIG. 8. The "concentration" (unit: %) indicated by a vertical axis of the graphs in FIGS. 8, 9, and 10 is standardized with a maximum concentration of each element being 100%. "A distance in the thickness direction" (unit: μm) indicated by a horizontal axis of the graphs in FIGS. 8, 9, and 10 is a thickness direction from a vicinity of an interface between the solder and the mounting electrode section toward the stretchable substrate. Note that, in the graphs in FIGS. 8, 9, and 10, the concentration distribution of silver (Ag), tin (Sn), and bismuth (Bi) is shown as a representative among the elements configuring the stretchable mounting board of Comparative Example 2.

As shown in the mapping diagram in FIG. 8, in the stretchable mounting board of Comparative Example 2, a boundary between the stretchable substrate and the stretchable wiring was determined, but a boundary between the stretchable wiring and the mounting electrode section was not determined.

As shown in the graph in FIG. 8, in the stretchable mounting board of Comparative Example 2, bismuth and tin in the solder diffused through the mounting electrode section into the stretchable wiring. That is, in the stretchable mounting board of Comparative Example 2, the diffusion of tin and bismuth could not be controlled by the mounting electrode section.

It was confirmed from the mapping diagram (focusing on tin) in FIG. 9 that tin in the solder diffused in the mounting electrode section and the stretchable wiring. Further, a state in which bismuth in the solder diffused in the mounting electrode section and the stretchable wiring was confirmed from the mapping diagram (focusing on bismuth) in FIG. 10.

<Evaluation 4>

A resistance of the stretchable wiring of the stretchable mounting boards of Comparative Example 2 was measured while changing an expansion ratio. For the measurement, a plurality of the stretchable mounting boards of Comparative Example 2 was used.

Figure 11:
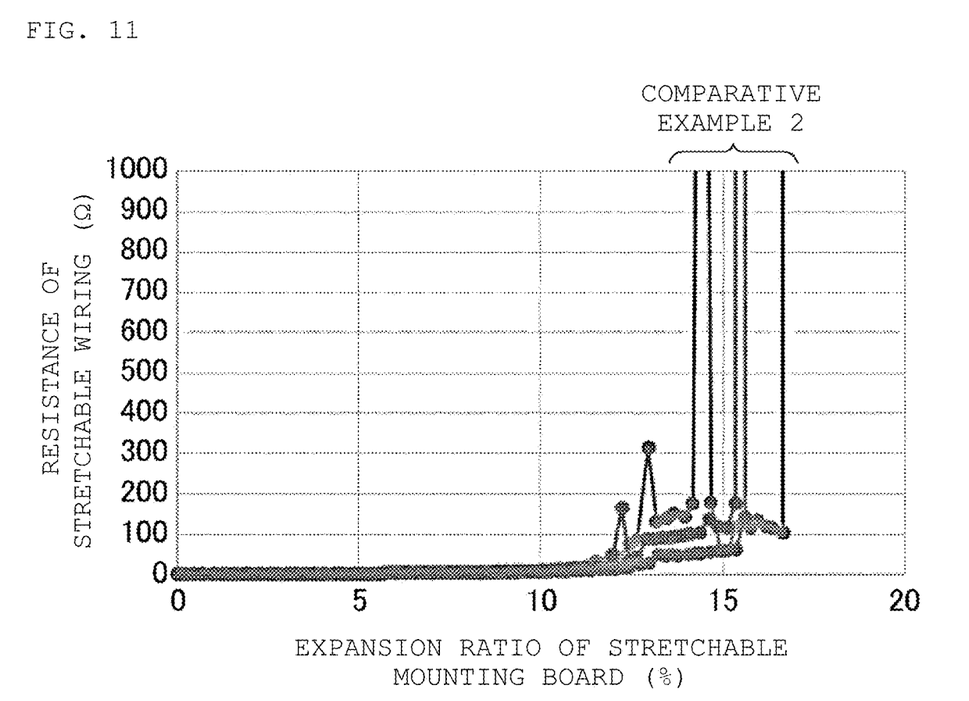
FIG. 11 is a graph showing a relationship between an expansion ratio and a resistance of the stretchable wiring in a stretchable mounting board of Comparative Example 2.

FIG. 11 is a graph showing a relationship between the expansion ratio and the resistance of the stretchable wiring in the stretchable mounting board of Comparative Example 2. Comparing FIGS. 7 and 11, a disconnection of the stretchable wiring when the stretchable mounting board expanded and contracted was not suppressed in the stretchable mounting board of Comparative Example 2 more than in the stretchable mounting board of Example 1. More specifically, as a range of the expansion ratio in which the stretchable wiring is not considered to be disconnected, the stretchable mounting board of Example 1 could expand to about 40%, whereas the stretchable mounting board of Comparative Example 2 could expand up to only about 15%.

DESCRIPTION OF REFERENCE SYMBOLS

1,2,3: Stretchable mounting board
10: Stretchable substrate
20: Stretchable wiring
30: Mounting electrode section
31: First electrode layer
32: Second electrode layer
40: Solder
50: Electronic component

The invention claimed is:
1. A stretchable mounting board comprising:
a stretchable substrate having a main surface;
a stretchable wiring disposed on the main surface of the stretchable substrate;
a mounting electrode section electrically connected to the stretchable wiring;

solder electrically connected to the mounting electrode section and including bismuth and tin; and an electronic component electrically connected to the mounting electrode section with the solder interposed between the electronic component and the mounting electrode, wherein the mounting electrode section has a first electrode layer on a side thereof facing the stretchable wiring and which includes bismuth and tin, and a second electrode layer on a side thereof facing the solder and which includes bismuth and tin, and a concentration of the bismuth in the first electrode layer is lower than a concentration of the bismuth in the second electrode layer.

2. The stretchable mounting board according to claim 1, wherein the mounting electrode section further includes silver and a resin.

3. The stretchable mounting board according to claim 2, wherein the resin includes at least one resin selected from an epoxy resin, a urethane resin, an acrylic resin, a silicone resin, and a polyester resin.

4. The stretchable mounting board according to claim 1, wherein a bismuth eutectic size in the second electrode layer is larger than a bismuth eutectic size in the first electrode layer.

5. The stretchable mounting board according to claim 4, wherein the bismuth eutectic size in the second electrode layer is 1 μm or more.

6. The stretchable mounting board according to claim 1, wherein the first electrode layer has a thickness of 5 μm or more.

7. The stretchable mounting board according to claim 1, wherein the second electrode layer has a thickness of 5 μm or more.

8. The stretchable mounting board according to claim 1, wherein a length of the first electrode layer is larger than a length of the second electrode layer.

9. The stretchable mounting board according to claim 1, wherein a length of the mounting electrode section is larger than a length of the solder.

10. The stretchable mounting board according to claim 1, wherein the stretchable wiring includes a mixture of conductive particles and a resin.

11. The stretchable mounting board according to claim 10, wherein the conductive particles are selected from silver, copper and nickel.

12. The stretchable mounting board according to claim 1, wherein the stretchable wiring includes silver and a resin.

13. The stretchable mounting board according to claim 12, wherein the resin includes at least one resin selected from an epoxy resin, a urethane resin, an acrylic resin, and a silicone resin.

14. The stretchable mounting board according to claim 1, wherein the stretchable substrate includes at least one resin selected from a silicone resin, an acrylic resin, an olefin resin, and a urethane resin.

15. The stretchable mounting board according to claim 14, wherein a bismuth eutectic size in the second electrode layer is larger than a bismuth eutectic size in the first electrode layer.

16. The stretchable mounting board according to claim 15, wherein the bismuth eutectic size in the second electrode layer is 1 μm or more.

17. The stretchable mounting board according to claim 14, wherein the first electrode layer has a thickness of 5 μm or more.

18. The stretchable mounting board according to claim 14, wherein the second electrode layer has a thickness of 5 μm or more.

19. The stretchable mounting board according to claim 14, wherein a length of the first electrode layer is larger than a length of the second electrode layer.

20. A stretchable mounting board comprising:

a stretchable substrate having a main surface;

a stretchable wiring disposed on the main surface of the stretchable substrate;

a first electrode layer electrically connected to the stretchable wiring, the first electrode layer including bismuth and tin; and a second electrode layer on the first electrode layer and arranged such that the first electrode layer is between the second electrode layer and the stretchable wiring, the second electrode layer including bismuth and tin, wherein a concentration of the bismuth in the first electrode layer is lower than a concentration of the bismuth in the second electrode layer.

* * * * *